United States Patent
Blum et al.

(10) Patent No.: US 6,316,617 B1
(45) Date of Patent: *Nov. 13, 2001

(54) CERTAIN AMIDO-AND AMINO-SUBSTITUTED BENZYLAMINE DERIVATIVES; A NEW CLASS OF NEUROPEPTIDE Y1 SPECIFIC LIGANDS

(75) Inventors: Charles A. Blum, Guilford; Robert DeSimone, Durham; Alan Hutchison, Madison; John M. Peterson, New Haven, all of CT (US)

(73) Assignee: Neurogen Corporation, Bradford, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 09/633,055

(22) Filed: Aug. 8, 2000

Related U.S. Application Data

(63) Continuation of application No. 08/897,046, filed on Jul. 18, 1997, now Pat. No. 6,133,265.
(60) Provisional application No. 60/022,298, filed on Jul. 23, 1996.

(51) Int. Cl.[7] ............ C07D 417/10; C07D 413/10; C07D 401/10; C07D 295/135; C07D 295/155
(52) U.S. Cl. ............ 544/60; 544/121; 544/235; 544/238; 544/353; 544/354; 544/357; 544/360; 544/365; 544/367; 544/368; 544/371; 544/372; 544/379; 544/393
(58) Field of Search .................. 544/393, 235, 544/371, 353, 354, 121, 360, 372, 60, 367, 379, 238, 368, 357, 365

(56) References Cited

U.S. PATENT DOCUMENTS

| | | | |
|---|---|---|---|
| 5,900,415 | 5/1999 | Peterson et al. | 514/252 |
| 5,962,455 | 10/1999 | Blum et al. | 514/252 |
| 5,985,873 | 11/1999 | Blum et al. | 514/235.8 |
| 6,133,265 | * 10/2000 | Blum et al. | 514/235.8 |

FOREIGN PATENT DOCUMENTS 9640660  12/1996  (WO).

OTHER PUBLICATIONS

Gehlert et al, Exp. Opin. Invest. Drugs 6 P 1827–1838 (1997).

Grundemar et al., TIPS, 15, P 153–159 (1994).

* cited by examiner

Primary Examiner—Emily Bernhardt

(57) ABSTRACT

This invention encompasses compounds of the formula

I

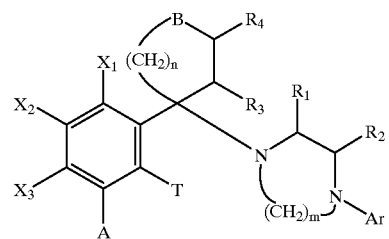

where $X_1$, $X_2$, and $X_3$, independently represent substituents of formula

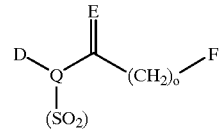

and the pharmaceutically acceptable salts thereof wherein
the remaining variables are as defined herein and wherein said compounds are useful in the diagnosis and treatment of feeding disorders such as obesity and bulimia and cardiovascular diseases such as essential hypertension and congestive heart failure due to the binding of these compounds to human Neuropeptide Y1 receptors.

16 Claims, No Drawings

CERTAIN AMIDO-AND AMINO-SUBSTITUTED BENZYLAMINE DERIVATIVES; A NEW CLASS OF NEUROPEPTIDE Y1 SPECIFIC LIGANDS

This application is a continuation of Ser. No. 08/897,046, filed Jul. 18, 1997, now U.S. Pat. No. 6,133,265, which claims the benefit of U.S. Provisional Patent Application No. 60/022,298, filed July 23, 1996.

BACKGROUND OF THE INVENTION

1. Field of the Invention

This invention relates to certain amide substituted benzylamine derivatives which selectively bind to mammalian Neuropeptide Y1 (NPY1) receptors. This invention also relates to pharmaceutical compositions comprising such compounds. It further relates to the use of such compounds and compositions in treating physiological disorders associated with an excess of Neuropeptide Y, especially feeding disorders and certain cardiovascular diseases.

2. Description of the Related Art

Neuropeptide Y, a peptide first isolated in 1982, is widely distributed in the central and peripheral neurons and is responsible for a multitude of biological effects in the brain and the periphery. Various animal studies have shown that activation of Neuropeptide $Y_1$ receptors is related to vasoconstriction, Wahlestedt et al., Regul. Peptides, 13: 307–318 (1986), McCauley and Westfall, J. Pharmacol. Exp. Ther. 261: 863–868 (1992), and Grundemar et al., Br. J. Pharmacol. 105: 45–50 (1992); and to stimulation of consummatory behavior, Flood and Morley, Peptides, 10: 963–966 (1989), Leibowitz and Alexander, Peptides, 12: 1251–1260 (1991), and Stanley et al., Peptides, 13: 581–587 (1992).

Grundemar and Hakanson, TiPS, May 1994 [Vol. 15], 153–159, state that, in animals, Neuropeptide Y is a powerful stimuli of food intake, and an inducer of vasoconstriction leading to hypertension. They further point out that low levels of Neuropeptide Y is associated with loss of appetite. These reports clearly indicate that compounds that inhibit the activity of this protein will reduce hypertension and appetite in animals.

BRIEF DESCRIPTION OF THE DRAWING

FIG. 1 shows representative substituted amido and amino substituted benzylamines of the present invention.

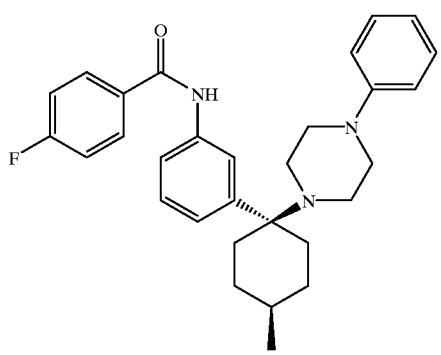

-continued

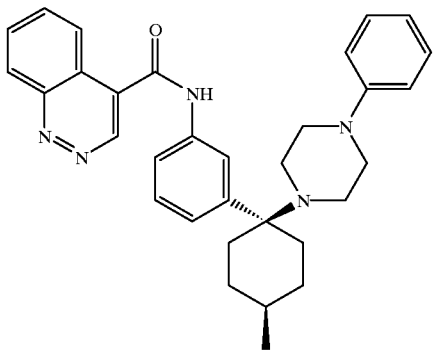

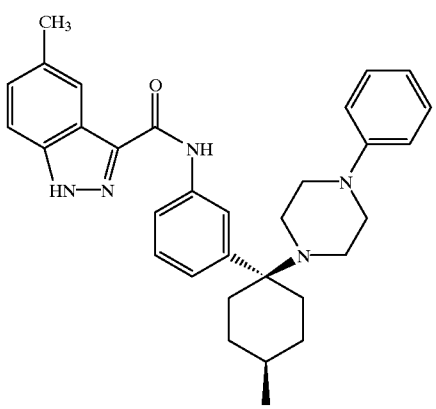

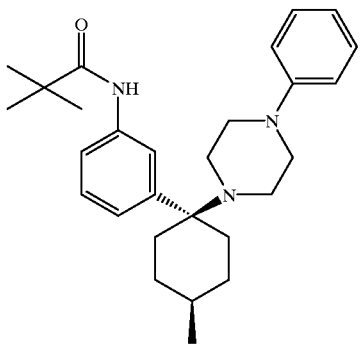

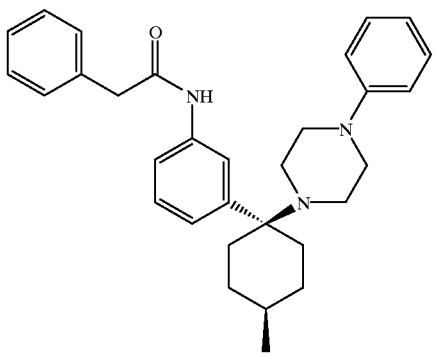

-continued

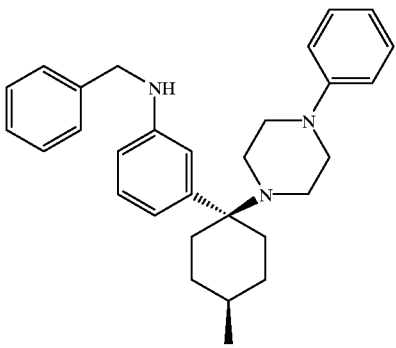

SUMMARY OF THE INVENTION

Compounds that interact with NPY1 receptors and inhibit the activity of Neuropeptide Y at those receptors are useful in treating physiological disorders associated with an excess of Neuropeptide Y. such as eating disorders for example, obesity and bulimia, and certain cardiovascular diseases, for example, hypertension.

This invention provides novel compounds of Formula I which selectively bind to Neuropeptide $Y_1$ (NPY1) receptors. Such compounds are useful in treating feeding disorders such as obesity and bulimia as well as certain cardiovascular diseases such as essential hypertension.

The compounds encompassed by the instant invention can be described by Formula I:

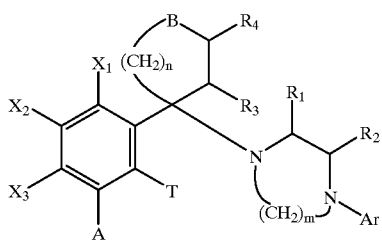

I wherein one of $X_1$, $X_2$, and $X_3$ is

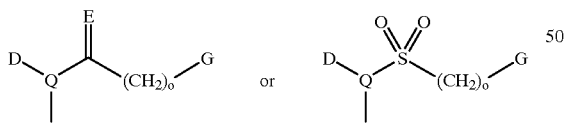

and the remaining members of the group $X_1$, $X_2$ and $X_3$ are hydrogen; and

Q=N or O;

D is absent when Q is O; when Q is N, D is H, lower straight or branched chain alkyl having 1–6 carbon atoms, a methylene unit incorporated into a ring connected with G (also a methylene) as in the cases of pyrrolidine, pyrrolidone, piperidine, and piperidone;

E=O or $H_2$;

o and r=0 or 1;

G=straight or branched chain lower alkyl having 1–6 carbon atoms, aryl, aryl substituted with halogen, straight or branched chain lower alkyl having 1–6 carbon atoms, heteroaryl—preferably selected from the group consisting of 2-, 3-, or 4-pyridyl, 2-pyrazyl, 2-, or 3-thienyl, 2-pyrazinyl, 2-, 3-, or 4-quinolyl, 1-, 3-, or 4-isoquinolyl, 2-quinoxalyl, 3-, or 4-cinnolyl, heteroaryl, each optionally substituted with halogen, hydroxy, straight or branched chain lower alkyl having 1–6 carbon atoms, straight or branched chain lower alkoxy having 1–6 carbon atoms;

Ar is an aryl group preferably selected from the group consisting of phenyl, 2-, 3-, or 4-pyridyl, 2- or 3-thienyl, 2-, 4- or 5-pyrimidyl, each of which is optionally mono- or disubstituted with halogen, hydroxy, or straight or branched chain lower alkyl having 1–6 carbon atoms;

B is sulfur, oxygen, $N(R_5)$ or $C(R_5)(R_6)$;

n is 1, 2 or 3;

m is 2, 3 or 4;

A and T are the same or different and represent hydrogen, halogen, hydroxy, straight or branched chain lower alkyl having 1–6 carbon atoms, or straight or branched chain lower alkoxy having 1–6 carbon atoms;

$R_1$ and $R_2$ are the same or different and represent hydrogen, or straight or branched chain lower alkyl having 1–6 carbon atoms;

$R_3$ and $R_4$ are the same or different and represent hydrogen, straight or branched chain lower alkyl having 1–6 carbon atoms, or straight or branched chain lower alkoxy having 1–6 carbon atoms;

$R_5$ represents hydrogen straight or branched chain lower alkyl having 1–6 carbon atoms, phenyl, 2-, 3-, or 4-pyridyl, or phenyl, 2-, 3-, or 4-pyridyl straight or branched chain lower alkyl having 1–6 carbon atoms; and A and $R_6$ are the same or different and represent hydrogen, hydroxyl, amino, straight or branched chain lower alkyl having 1–6 carbon atoms, straight or branched chain lower alkoxy having 1–6 carbon atoms, phenyl, 2-, 3-, or 4-pyridyl, phenoxy, 2-3-, or 4-pyridyloxy, or —$(CH_2)_p$—A'—$(CH_2)_q$—B' where p is 0–5, q is 1–5, and A' is a direct bond, oxygen or sulfur, and B' is hydrogen, straight or branched chain lower alkyl having 1–6 carbon atoms, straight or branched chain lower alkoxy having 1–6 carbon atoms, phenyl, 2-, 3-, or 4-pyridyl, phenoxy, 2-, 3-, or 4-pyridyloxy, carboxyl, carboalkoxy, carboxamido, mono or dialkylcarboxarnido, amino, or mono or dialkylarnino.

Preferred compounds according to Formula I are those where Ar is optionally substituted phenyl, pyrimidinyl or pyridyl, B is carbon optionally substituted with phenyl or alkyl, G is optionally substituted phenyl or heterocyclic amide or ester, and, A, T, and $R_1$–$R_4$ are hydrogen. Particularly, preferred compounds or Formula I are those where Ar is phenyl, pyrimidinyl or pyridyl, B is carbon optionally substituted with phenyl or alkyl, X is optionally substituted alkyl, phenyl, or heterocyclic amide, ester, or amine and A, T, and $R_1$–$R_4$ are hydrogen.

The invention also relates to compounds of Formula IA:

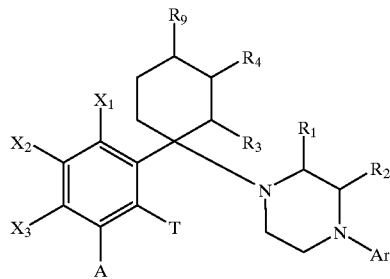

IA where
Ar is phenyl, 2-, 3-, or 4-pyridyl, 2- or 3-thienyl, 2-, 4- or 5-pyrimidyl, each of which is optionally mono- or disubstituted with halogen, hydroxy, or straight or branched chain lower alkyl having 1–6 carbon atoms;
one of $X_1$, and $X_2$ and $X_3$ is

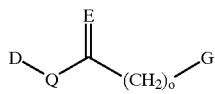

and the remaining members of the group of $X_1$ and $X_2$ and $X_3$ are hydrogen; and
Q=N or O;
D is absent when Q is O; where Q is N, D is H, lower straight or branched chain alkyl having 1–6 carbon atoms, a methylene unit incorporated into a ring connected with F (also a methylene) as in the cases of pyrrolidine, pyrrolidone, piperidine, and piperidone;
E=O or $H_2$;
o=0 or 1;
G=straight or branched chain lower alkyl having 1–6 carbon atoms, aryl, aryl substituted with halogen, straight or branched chain lower alkyl having 1–6 carbon atoms, heteroaryl—preferably selected from the group consisting of 2-, 3-, or 4-pyridyl, 2-pyrazyl, 2-, or 3-thienyl, 2-pyrazinyl, 2-, 3-, or 4-quinolyl, 1-, 3-, or 4-isoquinolyl, 2-quinoxalyl, 3-, or 4-cinnolyl, heteroaryl substituted with halogen, hydroxy, straight or branched chain lower alkyl having 1–6 carbon atoms, straight or branched chain lower alkoxy having 1–6 carbon atoms;
A and T are the same or different and represent hydrogen, halogen, hydroxy, straight-or branched chain lower alkyl having 1–6 carbon atoms, or straight or branched chain lower alkoxy having 1–6 carbon atoms;
$R_1$ and $R_2$ are the same or different and represent hydrogen, or straight or branched chain lower alkyl having 1–6 carbon atoms;
$R_3$ and $R_4$ are the same or different and represent hydrogen, straight or branched chain lower alkyl having 1–6 carbon atoms, or straight or branched chain lower alkoxy having 1–6 carbon atoms; and $R_9$ represents hydrogen, straight or branched chain lower alkyl having 1–6 carbon atoms, phenyl.
The invention further encompasses compounds of Formula II:

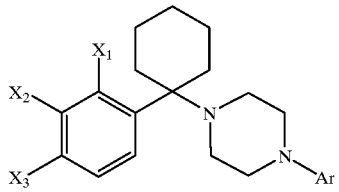

II where Ar represents phenyl, pyrimidinyl, or pyridyl one of $X_1$, $X_2$, and $X_3$ is

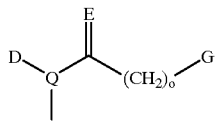

and the remaining members of the group of $X_1$, $X_2$, and $X_3$ are hydrogen; and
Q=N or O;
D is absent when Q=O; when Q is N, D is H, lower straight or branched chain alkyl having 1–6 carbon atoms, a methylene unit incorporated into a ring connected with G (also a methylene) as in the cases of pyrrolidine, pyrrolidone, piperidine, and piperidone;
E=O or $H_2$;
o=0 or 1;
G=straight or branched chain lower alkyl having 1–6 carbon atoms, aryl, aryl substituted with halogen, straight or branched chain lower alkyl having 1–6 carbon atoms, heteroaryl - preferably selected from the group consisting of 2-, 3-, or 4-pyridyl, 2-pyrazyl, 2-, or 3-thienyl, 2-pyrazinyl, 2-, 3-, or 4-quinolyl, 1or 4-isoquinolyl, 2-quinoxalyl, 3-, or 4-cinnolyl, heteroaryl substituted with halogen, hydroxy, straight or branched chain lower alkyl having 1–6 carbon atoms, straight or branched chain lower alkoxy having 1–6 carbon atoms.
Preferred compounds of Formula II are those where one of $X_1$, $X_2$, and $X_3$ is an alkyl amide having straight or branched chains of 1–6 carbon atoms or benzamide substituted with halogen, hydroxy, straight or branched chain lower alkyl having 1–6 carbon atoms, straight or branched chain lower alkoxy having 1–6 carbon atoms, or heterocyclic amides substituted with hydrogen, halogen, hydroxy, straight or branched chain lower alkyl having 1–6 carbon atoms, straight or branched chain lower alkoxy having 1–6 carbon atoms, and Ar represents phenyl, pyrimidinyl, or pyridyl.

The invention further includes compounds of Formula III:

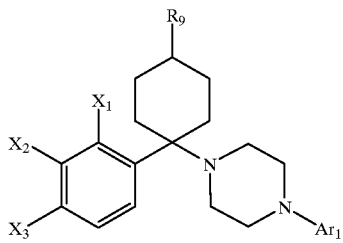

III where Ar, is phenyl, 2-, 3-, or 4-pyridyl, 2- or 3-thienyl, 2-, 4- or 5-pyrimidyl, each of which is optionally mono- or disubstituted with halogen, hydroxy, or straight or branched chain lower alkyl having 1–6 carbon atoms;

$R_9$ represents hydrogen, straight or branched chain lower alkyl having 1–6 carbon atoms, phenyl;

one of $X_1$, $X_2$, and $X_3$ is

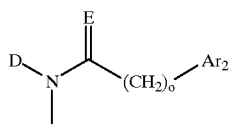

where
D=H or straight or branched lower alkyl having 1–6 carbon atoms;
E=O or $H_2$;
o=0 or 1;
Ar2 =phenyl or phenyl substituted with halogen, straight of branched chain lower alkyl having 1–6 carbon atoms, straight or branched chain lower alkyl having 1–6 carbon atoms, heteroaryl preferably selected from the group consisting of 1-, or 3-imidazolyl, 2-, 3-, or 4-pyridyl, 2-pyrazyl, 2-, or 3-thienyl, 2-pyrazinyl, 2-, 3-, or 4-quinolyl, 1-, 3-, or 4-isoquinolyl, 2-quinoxalyl, 3-, of 4-cinnolyl, 3-indazolyl, 3-benzoxalyl, 3-benzisoxazolyl, or the above heteroaryl substituted with halogen, hydroxy, straight or branched chain lower alkyl having 1–6 carbon atoms, straight or branched chain lower alkoxy having 1–6 carbon atoms;

The invention further includes compounds of Formula IV:

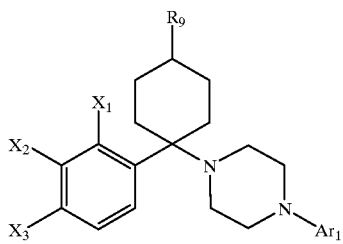

IV

Where $Ar_1$ is phenyl, 2-, 3-, or 4-pyridyl, 2- or 3-thienyl, 2-, 4- or 5-pyrimidyl, each of which is optionally mono- or disubstituted with halogen, hydroxy, or straight or branched chain lower alkyl having 1–6 carbon atoms;

$R_9$ represents hydrogen, straight or branched chain lower alkyl having 1–6 carbon atoms, phenyl;

one of $X_1$, $X_2$, and $X_3$ is

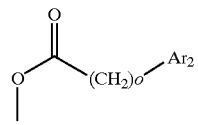

where
o 0 or 1;
Ar2 =phenyl or phenyl substituted with halogen, straight or branched chain lower alkyl having 1–6 carbon atoms, straight or branched chain lower alkyl having 1–6 carbon atoms, heteroaryl preferably selected from the group consisting of 1-, or 3-imidazolyl, 2-, 3-, or 4-pyridyl, 2-pyrazyl, 2-, or 3-thienyl, 2-pyrazinyl, 2-, 3-, or 4-quinolyl, 1-, 3-, or 4-isoquinolyl, 2-quinoxalyl, 3-, or 4-cinnolyl, 3-indazolyl, 3-benzoxalyl, 3-benzisoxazolyl, or the above heteroaryl substituted with halogen, hydroxy, straight or branched chain lower alkyl having 1–6 carbon atoms, straight or branched chain lower alkoxy having 1–6 carbon atoms;

The invention further includes compounds of Formula V:

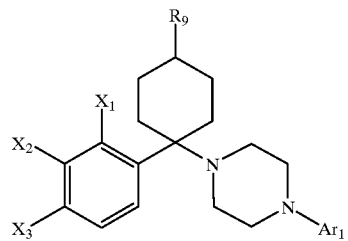

V where $Ar_1$ is phenyl, 2-, 3-, or 4-pyridyl, 2- or 3-thienyl, 2-, 4- or 5-pyrimidyl, each of which is optionally mono- or disubstituted with halogen, hydroxy, or straight or branched chain lower alkyl having 1–6 carbon atoms;

$R_9$ represents hydrogen, straight or branched chain lower alkyl having 1–6 carbon atoms, phenyl;

one of $X_1$, $X_2$, and $X_3$ is

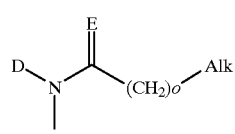

where
D=H or straight or branched lower alkyl having 1–6 carbon atoms;
E=0 or H2;
o=0 or 1;
Alk straight or branched chain lower alkyl having 1–6 carbon atoms, or straight or branched chain lower aminoalkyl or alkoxyalkyl having 1–6 carbon atoms.

The invention further includes compounds of Formula VI:

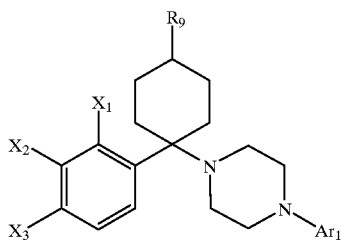

VI where Ar$_1$ is phenyl, 2-, 3-, or 4-pyridyl, 2- or 3-thienyl, 2-, 4- or 5-pyrimidyl, each of which is optionally mono- or disubstituted with halogen, hydroxy, or straight or branched chain lower alkyl having 1–6 carbon atoms;

R$_9$ represents hydrogen, straight or branched chain lower alkyl having 1–6 carbon atoms, phenyl;

one of X$_1$, X$_2$, and X$_3$ is

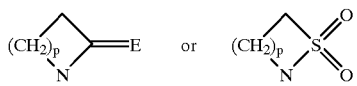

where
E=O or H$_2$;
p=1–3

The present invention also encompasses the acylated prodrugs of the compounds of Formula I–VIII. Those skilled in the art will recognize various synthetic methodologies which may be employed to prepare non-toxic pharmaceutically acceptable addition salts and acylated prodrugs of the compounds encompassed by Formula I.

The invention encompasses both diasteriomers of the compounds having 1,4- substitution on the cyclohexane ring. I.e, the invention encompasses both cis-, and trans-1, 4-cyclohexanes. Preferred compounds of the invention having 1,4-substitution on the cyclohexane ring are those where the nitrogen atom forming the piperazine ring and the alkyl or phenyl group in the 4-position of the cyclohexane ring are "cis" with respect to each other. Thus, preferred compounds of the invention having such substitution are those that are cis-1-piperazinyl-4-alkyl or phenyl-cyclohexanes.

DETAILED DESCRIPTION OF THE INVENTION

By "aryl" and "Ar" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which can optionally be unsubstituted or substituted with e.g., halogen, lower alkyl, lower alkoxy, lower alkylthio, trifluoromethyl, lower acyloxy, aryl, heteroaryl, and hydroxy.

By "alkyl" and "lower alkyl" is meant straight and branched chain alkyl groups having from 1–6 carbon atoms.

By "lower alkoxy" and "alkoxy" is meant straight and branched chain alkoxy groups having from 1–6 carbon atoms.

By "halogen" is meant fluorine, chlorine, bromine and iodine.

By 2-, 3-, and 4-pyridyloxy is meant groups of the following formulas respectively:

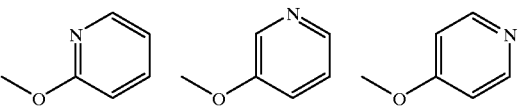

As the compounds of Formula I are effective Neuropeptide Y1 receptor antagonists, these compounds are of value in the treatment of a wide variety of clinical conditions which are characterized by the presence of an excess of Neuropeptide Y. Thus, the invention provides methods for the treatment or prevention of a physiological disorder associated with an excess of Neuropeptide Y, which method comprises administering to a mammal in need of said treatment an effective amount of a compound of Formula I or a pharmaceutically acceptable salt, solvate or prodrug thereof. The term "physiological disorder associated with an excess of Neuropeptide Y" encompasses those disorders associated with an inappropriate stimulation of Neuropeptide Y receptors, regardless of the actual amount of Neuropeptide Y present in the locale.

These physiological disorders may include:

disorders or diseases pertaining to the heart, blood vessels or the renal system, such as vasospasm, heart failure, shock, cardiac hypertrophy increased blood pressure, angina, myocardial infarction, sudden cardiac death, arrhythmia, peripheral vascular disease, and abnormal renal conditions such as impaired flow of fluid, abnormal mass transport, or renal failure;

conditions related to increased sympathetic nerve activity for example, during or after coronary artery surgery, and operations and surgery in the gastrointestinal tract;

cerebral diseases, and diseases related to the central nervous system, such as cerebral infarction, neurodegeneration, epilepsy, stroke, and conditions related to stroke, cerebral vasospasm and hemorrhage, depression, anxiety, schizophrenia, and dementia;

conditions related to pain or nociception;

diseases related to abnormal gastrointestinal motility and secretion, such as different forms of ileus, urinary incontinence, and Crohn's disease;

abnormal drink and food intake disorders, such as obesity, anorexia, bulimia, and metabolic disorders;

diseases related to sexual dysfunction and reproductive disorders;

conditions or disorders associated with inflammation;

respiratory diseases, such as asthma and conditions related to asthma and bronchoconstriction; and diseases related to abnormal hormone release, such as leutinizing hormone, growth hormone, insulin, and prolactin. See U. S. Pat. No. 5,504,094.

The pharmaceutical utility of compounds of this invention is indicated by the following assay for human NPY1 receptor activity.

Assay for Human NPY1 receptor binding activity

Compounds were assayed for activity using the following method:

Baculovirus-infected Sf9 cells expressing recombinant human NPY Y1 receptors were harvested at 42–48 hours at which time batches of 500 mL of cell suspension were pelleted by centrifugation. Each pellet was resuspended in 30 mL of lysis buffer (10 mM HEPES, 250 mM sucrose, 0.5 μg/ml leupeptin, 2 μg/ml Aprotonin, 200 μM PMSF and 2.5 mM EDTA, pH 7.4) and gently homogenized by 50 strokes using a dounce homogenizer. The homogenate was centrifuged at 4° C. for 10 minutes at 536×g to pellet the nuclei. The supernatant was collected into a fresh tube and centrifuged twice in the same buffer at 48,000×g for 40 minutes. The final pellet was resuspended in 10 mL of PBS containing 5 mM EDTA by dounce homogenization and stored in aliquots at −80° C.

Purified membranes were washed by PBS and resuspended by gentle pipetting in binding buffer (50 mM Tris (HCl), 5 mM KCl, 120 mM NaCl, 2 mM $CaCl_2$, 1 mM $MgCl_2$, 0.1% bovine serum albumin (BSA), pH 7.4). Membranes (5 μg) were added to siliconized (Sigmacote, Sigma) polypropylene tubes in addition to 0.050 nM [$^{125}$I]NPY (porcine) for competition analysis or 0.010–0.500 nM [$^{125}$I] NPY (porcine) for saturation analysis. For evaluation of guanine nucleotide effects on receptor affinity, GTP was added at a final concentration of 100 μM. Cold displacers were added at concentrations ranging from $10^{-12}$ M to $10^{-6}$ M to yield a final volume of 0.250 ml. Nonspecific binding was determined in the presence of 1 μM NPY(human) and accounted for less than 10% of total binding. Following a 2 hour incubation at room temperature, the reaction was terminated by rapid vacuum filtration. Samples were filtered over presoaked GF/C Whatman filters (1.0% polyethylenemine for 2 hours) and rinsed 2 times with 5 mLs cold binding buffer lacking BSA. Remaining bound radioactivity was measured by gamma counting. To estimate the Bmax, Kd and Ki, the results of binding experiments were analyzed using Sigmaplot software (Jandel).

The compounds of general formula 1 may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrastemal injection or infusion techniques. In addition, there is provided a pharmaceutical formulation comprising a compound of general Formula 1 and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soil capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soil gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserve by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

An illustration of the preparation of compounds of the present invention is given in Scheme I. Those having skill in the art will recognize that the starting materials may be varied and additional steps employed to produce compounds encompassed by the present invention.

Scheme 1

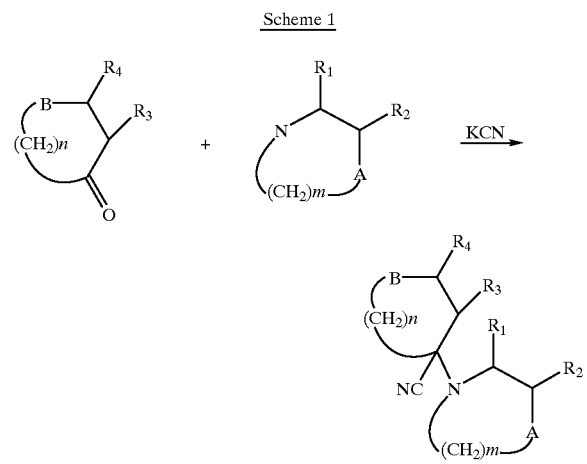

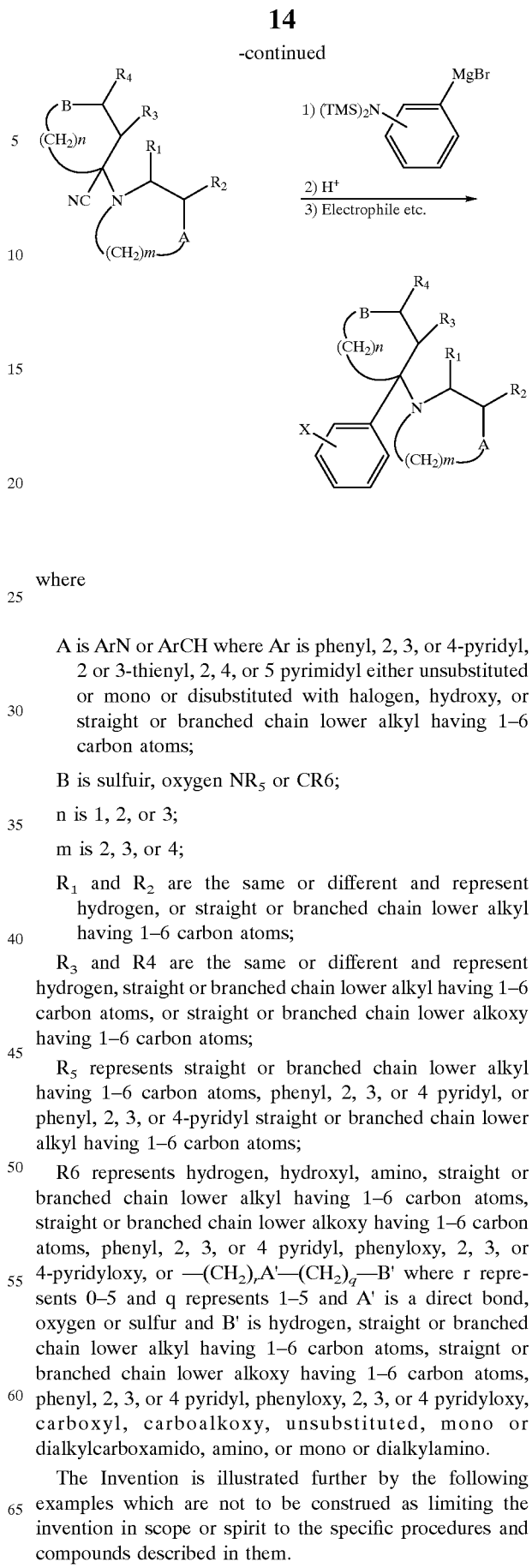

where

A is ArN or ArCH where Ar is phenyl, 2, 3, or 4-pyridyl, 2 or 3-thienyl, 2, 4, or 5 pyrimidyl either unsubstituted or mono or disubstituted with halogen, hydroxy, or straight or branched chain lower alkyl having 1–6 carbon atoms;

B is sulfuir, oxygen $NR_5$ or CR6;

n is 1, 2, or 3;

m is 2, 3, or 4;

$R_1$ and $R_2$ are the same or different and represent hydrogen, or straight or branched chain lower alkyl having 1–6 carbon atoms;

$R_3$ and R4 are the same or different and represent hydrogen, straight or branched chain lower alkyl having 1–6 carbon atoms, or straight or branched chain lower alkoxy having 1–6 carbon atoms;

$R_5$ represents straight or branched chain lower alkyl having 1–6 carbon atoms, phenyl, 2, 3, or 4 pyridyl, or phenyl, 2, 3, or 4-pyridyl straight or branched chain lower alkyl having 1–6 carbon atoms;

R6 represents hydrogen, hydroxyl, amino, straight or branched chain lower alkyl having 1–6 carbon atoms, straight or branched chain lower alkoxy having 1–6 carbon atoms, phenyl, 2, 3, or 4 pyridyl, phenyloxy, 2, 3, or 4-pyridyloxy, or —$(CH_2)_r$A'—$(CH_2)_q$—B' where r represents 0–5 and q represents 1–5 and A' is a direct bond, oxygen or sulfur and B' is hydrogen, straight or branched chain lower alkyl having 1–6 carbon atoms, straignt or branched chain lower alkoxy having 1–6 carbon atoms, phenyl, 2, 3, or 4 pyridyl, phenyloxy, 2, 3, or 4 pyridyloxy, carboxyl, carboalkoxy, unsubstituted, mono or dialkylcarboxamido, amino, or mono or dialkylamino.

The Invention is illustrated further by the following examples which are not to be construed as limiting the invention in scope or spirit to the specific procedures and compounds described in them.

EXAMPLE 1

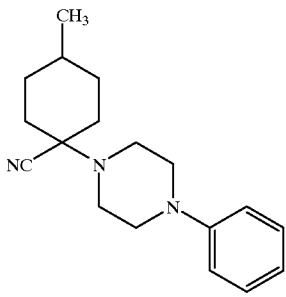

N-Phenylpiperazine (37 mL, 40 g, 245 mmol) was suspended in 300 mL water. The pH was adjusted to between 3 and 4 using 10% HCl. 4-Methyl cyclohexanone (30 mL, 27 g, 244 mmol) was added followed by KCN (16 g, 245 mmol). The mixture was stirred 15 hours at room temperature during which time the product solidified. The product was collected by filtration, washed with water, then dried in the vacuum oven overnight at 50° C. to give 58 g (84% yield) desired product as a roughly 2:1 mixture of diastereomers. Tlc Rf=0.25 and 0.3 (9:1, Hexanes/Ethyl Acetate).

EXAMPLE 2

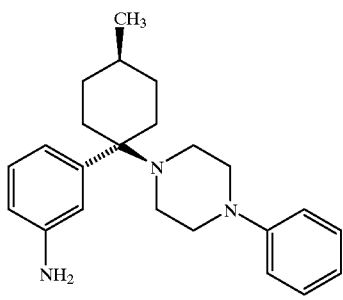

A 1 Molar THF solution of 3-[Bis(trimethylsilyl)amino] phenylmagnesium chloride (100 mL, 0.1 mol) was added to a solution of 1-cyano-1-(4-phenylpiperazine-1-yl)-4-methylcyclohexane (10 g, 0.035 mol) in dry THF (100 mL). The reaction mixture was heated to 65° C. for 2 h, cooled to room temperature and quenched by dropwise addition of saturated $NH_4Cl$ solution. The magnesium salts were filtered, rinsed with THF and the filtrate was concentrated under reduced pressure. The residue was dissolved in EtOH (70 mL), 5% HCl solution (20 mL) was added, and the mixture stirred for 30 min. at room temperature. The mixture was filtered and the filtrate was concentrated under reduced pressure. The residue was suspended in $H_2O$, made basic with 10 N NaOH and then extracted with EtOAc (3×). The combined extracts were washed with $H_2O$ (1×) and brine (1×), dried ($Na_2SO_4$), filtered and concentrated under reduced pressure. The residue was filtered through silica gel (1:4/EtOAc:hexanes) and concentrated to give a pale yellow solid. Recrystallization from isopropyl alcohol yielded white needles of 1-(3-aminophenyl)-1-(4-phenylpiperazine-1-yl)-4-methyl-cyclohexane (cis isomer) in 38% yield. mp=142–144° C.

EXAMPLEI 3

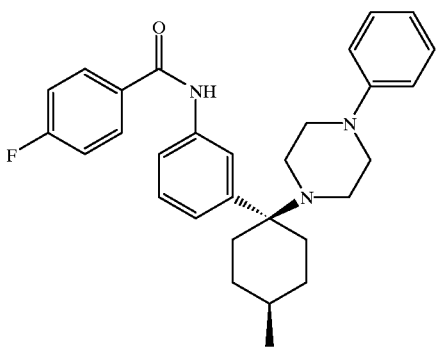

1-(3-Aminophenyl)-1-(4-phenylpiperazine-1-yl)-4-methyl-cyclohexane (cis isomer) (70 mg) was dissolved in 1 mL of pyridine at room temperature. 4-Dimethylamino pyridine (2 mg) was added followed by 4-fluorobenzoyl chloride (95 mg). The mixture was stirred for 2 hours. The mixture was then diluted with ethyl acetate and transferred to a separatory funnel. The solution wash washed 1×with saturated sodium bicarbonate solution, 1×with water, 3×saturated copper sulfate solution, and 1×water. The organic layer was then dried over sodium sulfate, filtered, and concentrated. The resulting solid was triturated with 80:20 hexanes:ethyl acetate to give 80 mg cis-N-[3-[4-methyl-1-(4-phenyl-1-piperazinyl) cyclohexyl]phenyl]-4-fluorobenzamide. m.p=210° C. (dec.)

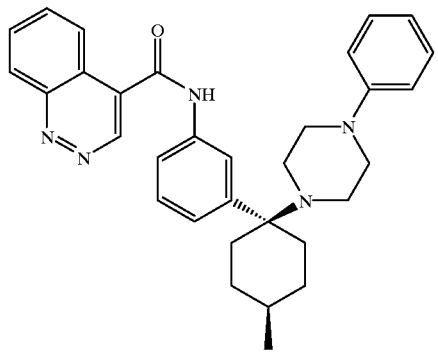

1-(3-Aminophenyl)-1-(4-phenylpiperazine-1-yl)-4-methyl-cyclohexane (cis isomer) (70 mg) and 4-cinnoline carboxylic acid (37 mg) were dissolved in 0.8 mL of dry DMF under a nitrogen atmosphere at room temperature. 1,3-Dicyclohexylcarbodiimide (43 mg) and 1-hydroxybenzotriazole (28 mg) were added. The mixture was stirred at room temperature for 2 days. The mixture was diluted with ethyl acetate and transferred to a separatory funnel. The solution was washed 2×with saturated sodium bicarbonate solution, 1×water, then 1×brine. The solution was dried over sodium sulfate, filtered, then concentrated. The residue was separated by flash chromatography eluting with 1:1 hexanes:ethyl acetate to give crude product as a yellow oil. This was further purified by preparative tlc eluting with 7:3 hexanes:ethyl acetate to afford cis-N-[3-[4-methyl-1-(4-phenyl-1-piperazinyl) cyclohexyl]phenyl]-4-cinnolinecarboxamide. m.p. (monohydrochloride)= 166–168° C.

EXAMPLE 5

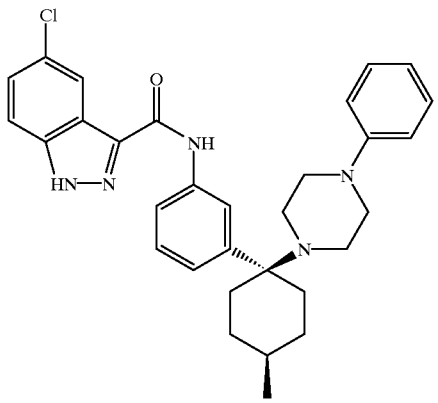

5-Chloroindazole-3-carboxylic acid (139 mg) was suspended in 1.5 mL of dry THF at room temperature under a nitrogen atmosphere. Enough dry DMF was added to solubilize the acid. The solution was cooled to 0° C. then triethylamine (216 mL) followed by ethylchloroformate (148 mL) was added. The mixture was stirred at 0° C. for 25 minutes after which time 1-(3-aminophenyl)-1-(4-phenylpiperazin-1-yl)-4-methyl cyclohexane (cis isomer) (250 mg) was added. The mixture was stirred for 12 hours allowing to warm to room temperature. The mixture was diluted with ethyl acetate and transferred to a separatory funnel. It was washed 3×with water then 1×with brine. The organic layer was dried over sodium sulfate, filtered, then concentrated. The residue was separated by preparative tlc eluting with 1:1 hexanes:ether and collecting the highest Rf band. This material was dissolved in 1 mL of ethanol with 1 mL 10% sodium hydroxide solution and heated at 80° C. for 10 minutes. The solvent was removed in vacuo to give the crude product as a pale yellow solid. This was washed with water then ether to give 5-chloro-cis-N-[3-[4-methyl-1-(4-phenyl-1-piperazinyl)cyclohexyl] phenyl]-1-H-indazol-3-carboxamide. m.p.=217–219° C.

EXAMPLE 6

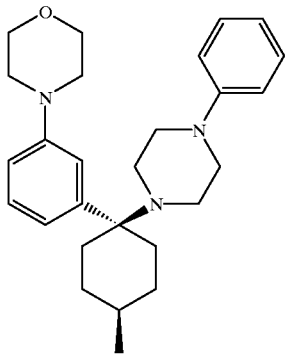

1-(3-Aminophenyl)-1-(4-phenylpiperazin-1-yl)-4-methyl cyclohexane (cis isomer) (150 mg) was dissolved in 1 mL dry DMF under a nitrogen atmosphere. 2-Bromoethyl ether (150 mg) and potassium carbonate (150 mg) were added and the mixture was heated to 90° C. for 6 hours. The mixture was cooled to room temperature, diluted with 20 mL ethyl acetate, and transferred to a separatory funnel. The mixture was washed 5×10 mL water and 1×10 mL brine. The organic phase was dried over sodium sulfate, filtered, and concentrated. The residue was purified by flash chromatography, eluting with 9/1 hexanes/ethyl acetate to give 68 mg 1-(3-morpholinophenyl)-1-(4-phenylpiperazin-1-1-yl)-4-methyl cyclohexane (cis isomer) as a clear oil. m.p. (HCl salt)= 178–180° C.

EXAMPLE 7

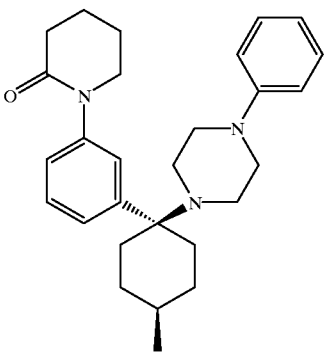

1-(3-Aminophenyl)-1-(4-phenylpiperazin-1-yl)-4-methyl cyclohexane (cis isomer) (105 mg) was dissolved in 1 mL dry THF at room temperature under a nitrogen atmosphere. 5-Chlorovaleryl chloride (56 mg) was added then N-methyl morpholine (46 mg). The mixture was stirred at room temperature for 90 minutes. Sodium hydride (36 mg of a 60 % oil dispersion) was added and the mixture was stirred 12 hours at 50° C. The mixture was cooled to room temperature, diluted with ethyl acetate, and transferred to a separatory funnel. The mixture was washed 1×water and 1×brine. The organic phase was dried over sodium sulfate, filtered, and concentrated. The residue was separated using flash chromatography eluting with 7/3 hexanes/ethyl acetate to give 114 mg 1-(3-piperidinonophenyl)-1-(4-phenylpiperazin-1-yl)-4-methyl cyclohexane (cis isomer) as a white solid. m.p. (HCl salt) 192–194° C.

EXAMPLE 8

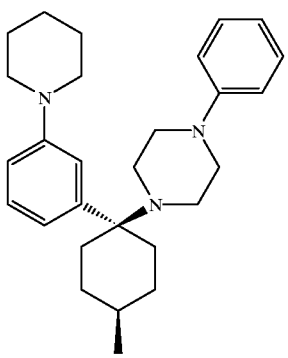

1-(3-Piperidinonophenyl)-1-(4-phenylpiperasin-1-yl)-4-methyl cyclohexane (cis isomer) (70 mg) was dissolved in 1.5 mnL dry THF at room temperature under a nitrogen atmosphere. Borane methyl sulfide complex (49 mL) was added and the mixture was refluxed for 12 hours. The mixture was cooled to room temperature and quenched with methanol. The solvent was removed in vacuo. To the residue was added 3 mL HCl saturated ethyl acetate. The solvent was removed, in vacuo. The residue was basified with concentrated ammonium hydroxide and transferred to a separatory funnel. This was extracted 2×5 mL ethyl acetate. The combined organic phases were washed 2×10 mL water then 1×10 mL brine. The organic phase was dried over sodium sulfate, filtered, then concentrated. The residue was separated using flash chromatography eluting with 9/1 hexanes/ethyl acetate to give 47 mg 1-(3-piperidinophenyl)-1-(4-phenyl piperazin-1-yl)-4-methyl cyclohexane (cis isomer). m.p (HCl salt)=174–176° C.

Preparation of Sulfonamides

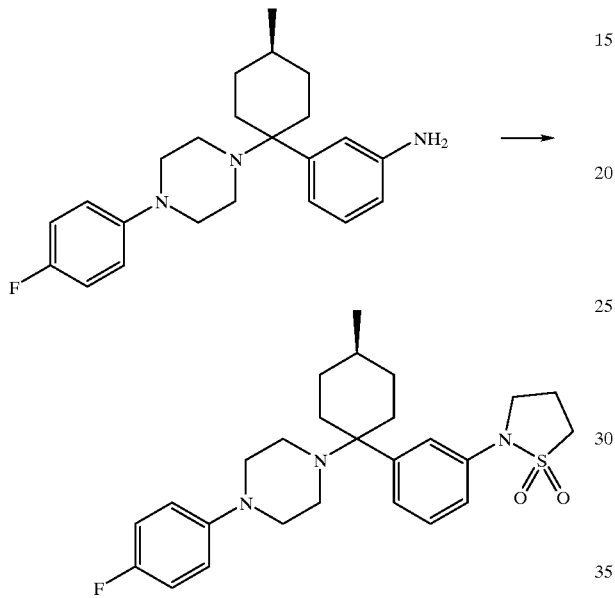

A solution of 1 (300 mg, 0.82 nunol), 3-chloropropylsulfonyl chloride (0.1 ml, 0.86 rnmol) and DMAP (105 mg, 0.86 mmol) in $CH_2Cl_2$ was stirred under a $N_2$ atmosphere at 23° C. for 2 h. The reaction mixture was concentrated under vacuum to dryness, then DMF (3 mL) and sodium hydride (67.2 mg, 1.78 mmol) were added. The reaction mixture was stirred for 1 hr at 23° C. and 3 hr at 65° C., cooled to 23° C. and diluted with EtOAc. The organic solution was washed with $H_2O$ (1×), sat'd aqueous $NaHCO_3$ and sat'd aqueous brine, dried ($MgSO_4$) and concentrated in vacuo to give a white solid. The crude residue was purified on a chromatotron (2 mm plate, 7:3 hexane/EtOAc solution) to give 148 mg of product as a colorless powder. MS (APCl): 472 (M+1); 1H NMR (400 MHz, CDCl3); d 7.1–6.55 (m, 8H), 4.8 (s, 2H), 3.6 (s, 2H), 3.0 (m, 4H), 2.5 (m, 6H), 1.6, 1.5, 0.97.

Additional compounds that may be prepared by the foregoing methods include:

Amido NPY Antagonists:

cis-N-[3-[4-methyl-1-(4-phenyl-1-piperazinyl)cyclohexyl]phenyl]-benzamide;

cis-N-[3-[4-methyl-1-(4-phenyl-1-piperazinyl)cyclohexyl]phenyl]-4-fluorobenzamide;

cis-N-[3-[4-methyl-1-(4-phenyl-1-piperazinyl)cyclohexyl]phenyl]-3-fluorobenzamide;

cis-N-[3-[4-methyl-1-(4-phenyl-1-piperazinyl)cyclohexyl]phenyl]-2-fluorobenzamide;

cis-N-[3-[4-methyl-1-(4-phenyl-1-piperazinyl)cyclohexyl]phenyl]-3,4-difluorobenzamide;

cis-N-[3-[4-methyl-1-(4-phenyl-1-piperazinyl)cyclohexyl]phenyl]-4-chlorobenzamide;

cis-N-[3-[4-methyl-1-(4-phenyl-1-piperazinyl)cyclohexyl]phenyl]-3-chlorobenzamide;

cis-N-[3-[4-methyl-1-(4-phenyl-1-piperazinyl)cyclohexyl]phenyl]-2-chlorobenzamide;

cis-N-[3-[4-methyl-1-(4-phenyl-1-piperazinyl)cyclohexyl]phenyl]-4-methoxybenzamide;

cis-N-[3-[4-methyl-1-(4-phenyl-1-piperazinyl)cyclohexyl]phenyl]-3-methoxybenzamide;

cis-N-[3-[4-methyl-1-(4-phenyl-1-piperazinyl)cyclohexyl]phenyl]-2-methoxybenzamide;

3-chloro-4-fluoro-cis-N-[3-[4-methyl-1-(4-phenyl-1-piperazinyl)-cyclohexyl]phenyl]-benzamide;

4-trifluoromethyl-cis-N-[3-[4-methyl-1-(4-phenyl-1-piperazinyl)cyclohexyl]phenyl]-benzamide;

2-fluoro-3-trifluoromethyl-cis-N-[3-[4-methyl-1-(4-phenyl-1-piperazinyl)cyclohexyl]phenyl]-benzamide;

3,5-bis-trifluoromethyl-cis-N-[3-[4-methyl-1-(4-phenyl-1-piperazinyl)cyclohexyl]phenyl]-benzamide;

2,4-dichloro-cis-N-[3-[4-methyl-1-(4-phenyl-1-piperazinyl)cyclohexyl]30 phenyl]-benzamide;

3-fluoro-4-methoxy-cis-N-[3-[4-methyl-1-(4-phenyl-1-piperazinyl)cyclohexyl]phenyl]-benzamide;

4-chloro-2-methoxy-cis-N-[3-[4-methyl-1-(4-phenyl-1-piperazinyl)cyclohexyl]phenyl]-benzamide;

2,3,4-trifluoro-cis-N-[3-[4-methyl-1-(4-phenyl-1-piperazinyl)cyclohexyl]phenyl]-benzamide;

2,4,5-trifluoro-cis-N-[3-[4-methyl-1-(4-phenyl-1-piperazinyl)cyclohexyl]phenyl]-benzamide;

2,3,6-trifluoro-cis-N-[3-[4-methyl-1-(4-phenyl-1-piperazinyl)cyclohexyl]phenyl]-benzamide;

cis-N-[3-[4-methyl-1-(4-phenyl-1-piperazinyl)cyclohexyl]phenyl]-4-trifluoromethylphenylacetamide;

cis-N-[3-[4-methyl-1-(4-phenyl-1-piperazinyl)cyclohexyl]phenyl]-2-pyridinecarboxamide;

cis-N-[3-[4-methyl-1-(4-phenyl-1-piperazinyl)cyclohexyl]phenyl]-3-pyridinecarboxamide;

cis-N-[3-[4-methyl-1-(4-phenyl-1-piperazinyl)cyclohexyl]phenyl]-4-pyridinecarboxamide;

cis-N-[3-[3-methyl-1-(4-phenyl-1-piperazinyl)cyclohexyl]phenyl]-2-pyridinecarboxamide;

cis-N-[3-[3-methyl-1-(4-phenyl-1-piperazinyl)cyclohexyl]phenyl]-3-pyridinecarboxamide;

cis-N-[3-[3-methyl-1-(4-phenyl-1-piperazinyl)cyclohexyl]phenyl]-4-pyridinecarboxamide;

2,6-dimethoxy-cis-N-[3-[4-methyl-1-(4-phenyl-1-piperazinyl)cyclohexyl]phenyl]-3-pyridinecarboxamide;

5,6-dichloro-cis-N-[3-[4-methyl-1-(4-phenyl-1-piperazinyl)cyclohexyl]phenyl]-3-pyridinecarboxamide;

2,6-dichloro-cis-N-[3-[4-methyl-1-(4-phenyl-1-piperazinyl)cyclohexyl]phenyl]-3-pyridinecarboxarnide;

5-chloro-1,6-dihydro-cis-N-[3-[4-methyl-1-(4-phenyl-1-piperazinyl)cyclohexyl]phenyl]-6-oxo-3-pyridinecarboxamide;

1,6-dihydro-cis-N-[3-[4-methyl-1-(4-phenyl-1-piperazinyl)cyclohexyl]phenyl]-6-oxo-3-pyridinecarboxamide;

1,6-dihydro-cis-N-[3-[4-methyl-1-(4-phenyl-1-piperazinyl)cyclohexyl]phenyl]-2-oxo-3-pyridinecarboxamide;

cis-N-[3-[4-methyl-1-(4-phenyl-1-piperazinyl)cyclohexyl]phenyl]-(2-methyl)-4-pyridinecarboxamide;

cis-N-[3-[4-methyl-1-(4-phenyl-1-piperazinyl)cyclohexyl]phenyl]-(3-methyl)-4-pyridinecarboxamide;

cis-N-methyl-N-[3-[4-methyl-1-(4-phenyl-1-piperazinyl)cyclohexyl]phenyl]-4-pyridinecarboxamide;

cis-N-methyl-N-[3-[4-methyl-1-(4-phenyl-1-piperazinyl)cyclohexyl]phenyl]-(3-methyl)-4-pyridinecarboxamide;

cis-N-[3-[4-methyl-1-(4-phenyl-1-piperazinyl)cyclohexyl]phenyl]-3-thiophenecarboxamide;

cis-N-[3-[3-methyl-1-(4-phenyl-1-piperazinyl)cyclohexyl]phenyl]-2-thiophenecarboxamide;

cis-N-[3-[3-methyl-1-(4-phenyl-1-piperazinyl)cyclohexyl]phenyl]-3-furancarboxamide;

cis-N-[3-[3-methyl-1-(4-phenyl-1-piperazinyl)cyclohexyl]phenyl]-4-cinnolinecarboxamide;

cis-N-[3-[4-methyl-1-(4-phenyl-1-piperazinyl)cyclohexyl]phenyl]-4-quinolinecarboxamide;

cis-N-[3-[4-methyl-1-(4-phenyl-1-piperazinyl)cyclohexyll-3-quinolinecarboxamide;

cis-N-[3-[4-methyl-1-(4-phenyl-1-piperazinyl)cyclohexyl]phenyl]-2-quinolinecarboxamide;

4-hydroxy-cis-N-[3-[4-methyl-1-(4-phenyl-1-piperazinyl) cyclohexyl]phenyl]-3-cinnolinecarboxamide;

7-trifluoromethyl-4-hydroxy-cis-N-[3-[4-methyl-1-(4-phenyl-1-piperazinyl)cyclohexyl]phenyl]-3-quinolinecarboxamide;

4-hydroxy-cis-N-[3-[4-methyl-1-(4-phenyl-1-piperazinyl)cyclohexyl]phenyl]-3-quinolinecarboxamide;

cis-N-[3-[4-methyl-1-(4-phenyl-1-piperazinyl)cyclohexyl]phenyl]-3-isoquinolinecarboxamide;

cis-N-[3-[4-methyl-1-(4-phenyl-1-piperazinyl)cyclohexyl]phenyl]-1-naphthalenecarboxamide;

cis-N-[3-[4-methyl-1-(4-phenyl-1-piperazinyl)cyclohexyl]phenyl]-2-naphthalenecarboxamide;

cis-N-[3-[4-methyl-1-(4-phenyl-1-piperazinyl)cyclohexyl]phenyl]-2-quinoxalinecarboxamide;

cis-N-[3-[4-methyl-1-(4-phenyl-1-piperazinyl)cyclohexyl]phenyl]-2-pyridylacetylcarboxarnide;

cis-N-[3-[4-methyl-1-(4-phenyl-1-piperazinyl)cyclohexyl]phenyl]-3-pyridylacetylcarboxamide;

cis-N-[3-[4-methyl-1-(4-phenyl-1-piperazinyl)cyclohexyl]phenyl]-4-pyridylacetylcarboxamnide;

cis-N-[3-[4-methyl-1-(4-phenyl-1-piperazinyl)cyclohexyl]phenyl]-3-thienylacetylcarboxamide;

cis-N-[3-[4-methyl-1-(4-phenyl-1-piperazinyl)cyclohexyl]phenyl]morpholinoacetylcarboxamide;

cis-N-[3-[4-methyl-1-(4-phenyl-1-piperazinyl)cyclohexyl]phenyl]thiomorpholioacetylcarboxamide;

cis-N-[3-[4-methyl-1-(4-phenyl-1-piperazinyl)cyclohexyl]phenyl]-4-methyl-1-piperazinylacetylcarboxamide;

cis-N-[3-[4-methyl-1-(4-phenyl-1-piperazinyl)cyclohexyl]phenyl]trimethylacetylcarboxamide;

cis-N-[3-[4-methyl-1-(4-phenyl-1-piperazinyl)cyclohexyl]phenyl]-4-pyrazolocarboxamide;

cis-N-[3-[4-methyl-1-(4-phenyl-1-piperazinyl)cyclohexyl]phenyl]-4-pyridazinylcarboxamide;

4-methyl-cis-N-[3-[3-methyl-1-(4-phenyl-1-piperazinyl)cyclohexyl]phenyl]-3-pyridazinylcarboxamide;

cis-N-[3-[4-methyl-1-(4-phenyl-1-piperazinyl)cyclohexyllphenyl]-2-pyridazinylcarboxamide;

5-methyl-cis-N-[3-[4-methyl-1-(4-phenyl-1-piperazinyl)cyclohexyl]phenyl]-2-pyridazinylcarboxamide;

cis-N-[3-[4-methyl-1-(4-phenyl-1-piperazinyl)cyclohexyl]phenyl]-4-(3-methylpyridazinyl)carboxamide;

cis-N-[3-[4-methyl-1-(4-phenyl-1-piperazinyl)cyclohexyl]phenyl]-2-pyrazinylcarboxamide;

cis-N-[3-[4-methyl-1-(4-phenyl-1-piperazinyl)cyclohexyl]phenyl]-4-nitrobenzamide;

cis-N-[3-[4-methyl-1-(4-phenyl-1-piperazinyl)cyclohexyl]phenyl]-4-aminobenzamide;

cis-N-[3-[4-methyl-1-(4-phenyl-1-piperazinyl)cyclohexyl]phenyl]-1,2-benzisoxazole-3-carboxamide;

trans-N-[3-[3-methyl-1-(4-phenyl-1-piperazinyl)cyclohexyl]phenyl]-1,2-benzisoxazole-3-carboxamide;

trans-N-[3-[3-methyl-1-(4-(4-fluoropheny)-1-piperazinyl)cyclohexyl]phenyl]-1,2-benzisoxazole-3-carboxamide;

cis-N-[3-[4-methyl-1-(4-(4-fluoropheny)-1-piperazinyl)cyclohexyl]phenyl]-1,2-benzisoxazole-3-carboxamide;

cis-N-[3-[4-methyl-1-(4-(4-fluoropheny)-1-piperazinyl)cyclohexyl]phenyl]-4-cinnolinecarboxamide;

trans-N-[3-[3-methyl-1-(4-(4-fluoropheny)-1-piperazinyl) cyclohexyl]phenyl]-4-cinnolinecarboxamide;

cis-5-chloro-N-[3-[4-methyl-1-(4-phenyl-1-piperazinyl)cyclohexyl]phenyl]-1H-indazole-3-carboxamide;

cis-5-chloro-N-[3-[4-methyl-1-(4-(4-flurophenyl-1-piperazinyl)cyclohexyl]phenyl]-1H-indazole-3-carboxamide;

cis-N-[3-[4-methyl-1-(4-phenyl-1-piperazinyl)cyclohexyl]phenyl]-1H-indazole-3-carboxamide;

trans-N-[3-[3-methyl-1-(4-phenyl-1-piperazinyl)cyclohexyl]phenyl]-1H-indazole-3-carboxamide;

cis-N-[3-[4-methyl-1-(4-(4-fluorophenyl-1-piperazinyl)cyclohexyl]phenyl]-2-quinoxalinecarboxamide;

cis-N-[3-[4-methyl-1-(4-phenyl-1-piperazinyl)cyclohexyl]phenyl]-1H-indole-3-carboxamide;

cis-5-chloro-N-[3-[4-methyl-1-(4-phenyl-1-piperazinyl)cyclohexyl]phenyl]-1H-indole-3-carboxamide;

cis-5-methyl-N-[3-[4-methyl-1-(4-(4-fluorophenyl-1-piperazinyl) cyclohexyl]phenyl]-1H-indazole-3-carboxamide;

cis-5-chloro-N-[3-[4-methyl-1-(4-phenyl-1-piperazinyl)cyclohexyl]phenyl]-1,2-benzisoxazole-3-carboxamide;

cis-5-chloro-N-[3-[4-methyl-1-(4-(4-flurophenyl)-1-piperazinyl)cyclohexyl]phenyl]-1,2-benzisoxazole-3-carboxamide;

trans-N-[3-[3-methyl-1-(4-phenyl-1-piperazinyl)cyclohexyl]phenyl]-1,2-benzisoxazole-3-carboxamide;

Sulfonamido NPY Antagonists cis-N-[3-[4-methyl-1-(4-phenyl-1-piperazinyl)cyclohexyllphenyl]-2-naphthalenesulfonamide;

cis-N-[3-[4-methyl-1-(4-phenyl-1-piperazinyl)cyclohexyl]phenyl]-methanesulfonamide;

cis-N-[3-[4-methyl-1-(4-phenyl-1-piperazinyl) cyclohexyl]phenyl]-toluenesulfonamide.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. An amido NPY antagonist selected from the group consisting of
   cis-N-{3-[4-methyl-1-(4-phenyl-1-piperazinyl) cyclohexyl]phenyl }-4-fluorobenzamide.

2. An amido NPY antagonist selected from the group consisting of:
   cis-N-[3-[4-methyl-1-(4-phenyl-1-piperazinyl) cyclohexyl]phenyl]-benzamide;
   cis-N-[3-[4-methyl-1-(4-phenyl-1-piperazinyl) cyclohexyl]phenyl]-4-fluorobenzamide;
   cis-N-[3-[4-methyl-1-(4-phenyl-1-piperazinyl) cyclohexyl]phenyl]-3-fluorobenzamide;
   cis-N-[3-[4-methyl-1-(4-phenyl-1-piperazinyl) cyclohexyl]phenyl]-2-fluorobenzamide;
   cis-N-[3-[4-methyl-1-(4-phenyl-1-piperazinyl) cyclohexyl]phenyl]-3,4-difluorobenzamide;
   cis-N-[3-[4-methyl-1-(4-phenyl-1-piperazinyl) cyclohexyl]phenyl]-4-chlorobenzamide;
   cis-N-[3-[4-methyl-1-(4-phenyl-1-piperazinyl) cyclohexyl]phenyl]-3-chlorobenzamide;
   cis-N-[3-[4-methyl-1-(4-phenyl-1-piperazinyl) cyclohexyl]phenyl]-2-chlorobenzamide;
   cis-N-[3-[4-methyl-1-(4-phenyl-1-piperazinyl) cyclohexyl]phenyl]-4-methoxybenzamide;
   cis-N-[3-[4-methyl-1-(4-phenyl-1-piperazinyl) cyclohexyl]phenyl]-3-methoxybenzamide;
   cis-N-[3-[4-methyl-1-(4-phenyl-1-piperazinyl) cyclohexyl]phenyl]-2-methoxybenzamide;
   3-chloro-4-fluoro-cis-N-[3-[4-methyl-1-(4-phenyl-1-piperazinyl) cyclohexyl]phenyl]-benzamide;
   4-trifluoromethyl-cis-N-[3-[4-methyl-1-(4-phenyl-1-piperazinyl) cyclohexyl]phenyl]-benzamide;
   2-fluoro-3-trifluoromethyl-cis-N-[3-[4-methyl-1-(4-phenyl-1-piperazinyl)cyclohexyl]phenyl]-benzamide;
   3,5-bis-trifluoromethyl-cis-N-[3-[4-methyl-1-(4-phenyl-1-piperazinyl) cyclohexyl]phenyl]-benzamide;
   2,4-dichloro-cis-N-[3-[4-methyl-1-(4-phenyl-1-piperazinyl)cyclohexyl]phenyl]-benzamide;
   3-fluoro-4-methoxy-cis-N-[3-[4-methyl-1-(4-phenyl-1-piperazinyl) cyclohexyl]phenyl]-benzamide;
   4-chloro-2-methoxy-cis-N-[3-[4-methyl-1-(4-phenyl-1-piperazinyl) cyclohexyl]phenyl]-benzamide;
   2,3,4-trifluoro-cis-N-[3-[4-methyl-1-(4-phenyl-1-piperazinyl) cyclohexyl]phenyl]-benzamide;
   2,4,5-trifluoro-cis-N-[3-[4-methyl-1-(4-phenyl-1-piperazinyl) cyclohexyl]phenyl]-benzamide; and
   2,3,6-trifluoro-cis-N-[3-[4-methyl-1-(4-phenyl-1-piperazinyl) cyclohexyl]phenyl]-benzamide.

3. An amido NPY antagonist selected from the group consisting of:
   cis-N-[3-[4-methyl-1-(4-phenyl-1-piperazinyl) cyclohexyl]phenyl]-2-pyridinecarboxamide;
   cis-N-[3-[4-methyl-1-(4-phenyl-1-piperazinyl) cyclohexyl]phenyl]-3-pyridinecarboxamide;
   cis-N-[3-[4-methyl-1-(4-phenyl-1-piperazinyl) cyclohexyl]phenyl]-4-pyridinecarboxamide;
   cis-N-[3-[3-methyl-1-(4-phenyl-1-piperazinyl) cyclohcxyl]phenyl]-2-pyridinecarboxamide;
   cis-N-[3-[3-methyl-1-(4-phenyl-1-piperazinyl) cyclohexyl]phenyl]-3-pyridinecarboxamide;
   cis-N-[3-[3-methyl-1-(4-phenyl-1-piperazinyl) cyclohexyl]phenyl]-4-pyridinecarboxamide;
   2,6-dimethoxy-cis-N-[3-[4-methyl-1-(4-phenyl-1-piperazinyl) cyclohexyl]phenyl]-3-pyridinecarboxamide;
   5,6-dichloro-cis-N-[3-[4-methyl-1-(4-phenyl-1-piperazinyl) cyclohexyl]phenyl]-3-pyridinecarboxamide;
   2,6-dichloro-cis-N-[3-[4-methyl-1-(4-phenyl-1-piperazinyl) cyclohexyl]phenyl]-3-pyridinecarboxamide;
   5-chloro-1,6-dihydro-cis-N-[3-[4-methyl-1-(4-phenyl-1-piperazinyl) cyclohexyl]phenyl]-6-oxo-3-pyridinecarboxamide;
   1,6-dihydro-cis-N-[3-[4-methyl-1-(4-phenyl-1-piperazinyl)cyclohexyl]phenyl]-6-oxo-3-pyridinecarboxamide;
   1,6-dihydro-cis-N-[3-[4-methyl-1-(4-phenyl-1-piperazinyl)cyclohexyl]phenyl]-2-oxo-3-pyridinecarboxamide;
   cis-N-[3-[4-methyl-1-(4-phenyl-1-piperazinyl) cyclohexyl]phenyl]-(2-methyl)-4-pyridinecarboxamide;
   cis-N-[3-[4-methyl-1-(4-phenyl-1-piperazinyl) cyclohexyl]phenyl]-(3-methyl)-4-pyridinecarboxamide;
   cis-N-methyl-N-[3-[4-methyl-1-(4-phenyl-1-piperazinyl) cyclohexyl]phenyl]-4-pyridinecarboxamide; and
   cis-N-methyl-N-[3-[4-methyl-1-(4-phenyl-1-piperazinyl) cyclohexyl]phenyl]-(3-methyl)-4-pyridinecarboxamide.

4. An amido NPY antagonist selected from the group consisting of:
   cis-N-[3-[4-methyl-1-(4-phenyl-1-piperazinyl) cyclohexyl]phenyl]-3-thiophenecarboxamide;
   cis-N-[3-[3-methyl-1-(4-phenyl-1-piperazinyl) cyclohexyl]phenyl]-2-thiophenecarboxamide; and
   cis-N-[3-[3-methyl-1-(4-phenyl-1-piperazinyl) cyclohexyl]phenyl]-3-furancarboxamide.

5. An amido NPY antagonist selected from the group consisting of:
   cis-N-[3-[4-methyl-1-(4-phenyl-1-piperazinyl) cyclohcxyl]phenyl]-4-quinolinecarboxamide;
   cis-N-[3-[4-methyl-1-(4-phenyl-1-piperazinyl) cyclohexyl]phenyl]-3-quinolinecarboxamide;
   cis-N-[3-[4-methyl-1-(4-phenyl-1-piperazinyl) cyclohexyl]phenyl]-2-quinolinecarboxamide;
   7-trifluoromethyl-4-hydroxy-cis-N-[3-[4-methyl-1-(4-phenyl-1-piperazinyl)cyclohexyl]phenyl]-3-quinolinecarboxamide;
   4-hydroxy-cis-N-[3-[4-methyl-1-(4-phenyl-1-piperazinyl) cyclohexyl]phenyl]-3-quinolinecarboxamide; and cis-N-[3-[4-methyl-1-(4-phenyl-1-piperazinyl) cyclohexyl]phenyl]-3-isoquinolinecarboxamide.

6. An amido NPY antagonist selected from the group consisting of
cis-N-[3-[3-methyl-1-(4-phenyl-1-piperazinyl) cyclohexyl]phenyl]-4-cinnolinecarboxamide;
4-hydroxy-cis-N-[3-[4-methyl-1-(4-phenyl-1-piperazinyl)cyclohexyl]phenyl]-3-cinnolinecarboxamide; and
cis-N-[3-[4-methyl-1-(4-(4-fluorophenyl)-1-piperazinyl) cyclohexyl]phenyl]-4-cinnolinecarboxamide; and
trans-N-[3-[3-methyl-1-(4-(4-fluorophenyl)-1-piperazinyl)cyclohexyl]phenyl]-4-cinnolinecarboxamide.

7. An amido NPY antagonist selected from the group consisting of:
cis-N-[3-[4-methyl-1-(4-phenyl-1-piperazinyl) cyclohexyl]phenyl]-2-pyridylacetylcarboxamide;
cis-N-[3-[4-methyl-1-(4-phenyl-1-piperazinyl) cyclohexyl]phenyl]-3-pyridylacetylcarboxamide;
cis-N-[3-[4-methyl-1-(4-phenyl-1-piperazinyl) cyclohexyl]phenyl]-4-pyridylacetylcarboxamide;
cis-N-[3-[4-methyl-1-(4-phenyl-1-piperazinyl) cyclohexyl]phenyl]-3-thienylacetylcarboxamide;
cis-N-[3-[4-methyl-1-(4-phenyl-1-piperazinyl) cyclohexyl]phenyl]morpholinoacetylcarboxamide;
cis-N-[3-[4-methyl-1-(4-phenyl-1-piperazinyl) cyclohexyl]phenyl]thiomorpholinoacetylcarboxamide;
cis-N-[3-[4-methyl-1-(4-phenyl-1-piperazinyl) cyclohexyl]phenyl]-4) methyl-1-piperazinylacetylcarboxamide;
cis-N-[3-[4-methyl-1-(4-phenyl-1-piperazinyl) cyclohexyl]phenyl]trimethylacetylcarboxamide; and
cis-N-{3-[4-methyl1-(4-phenyl-1-piperazinyl) cyclohexyl]phenyl}-4-trimethylphenylacetamide.

8. An amido NPY antagonist selected from the group consisting of:
cis-N-[3-[4-methyl-1-(4-phenyl-1-piperazinyl) cyclohexyl]phenyl]-4-pyridazinylcarboxamide;
4-methyl-cis-N-[3-[3-methyl1-(4-phenyl-1-piperazinyl) cyclohcxyl]phenyl]-3-pyridazinylcarboxamide;
cis-N-[3-[4-methyl-1-(4-phenyl-1-piperazinyl) cyclohexyl]phenyl]-2-pyridazinylcarboxamide;
5-methyl-cis-N-[3-[4-methyl-1-(4-phenyl-1-piperazinyl) cyclohexyl]phenyl]-2-pyridazinylcarboxamide; and
cis-N-[3-[4-methyl-1-(4-phenyl-1-piperazinyl) cyclohexyl]phenyl]-4-(3-methylpyridazinyl) carboxamide.

9. An amido NPY antagonist selected from the group consisting of:
cis-N-[3-[4-methyl-1-(4-phenyl-1-piperazinyl) cyclobexyl]phenyl]-1,2-benzisoxazole-3-carboxamide;
trans-N-[3-[3-methyl-1-(4-phenyl-1-piperazinyl) cyclohexyl]phenyl]-1,2-benzisoxazole-3-carboxamide;
trans-N-[3-[3-methyl-1-(4-(4-fluorophenyl)-1-piperazinyl)cyclohexyl]phenyl]-1,2-benzisoxazole-3-carboxamide;
cis-N-[3-[4-methyl-1-(4-(4-fluorophenyl)-1-piperazinyl) cyclohexyl]phenyl]-1, 2-benzisoxazole-3-carboxamide; and
cis-5-chloro-N-[3-[4-methyl1-(4-phenyl-1-piperazinyl) cyclohexyl]phenyl]-1,2-benzisoxazole-3-carboxamide;
cis-5-chloro-N-[3-[4-methyl-1-(4-(4-flurophenyl)-1-piperazinyl) cyclohexyl]phenyl]-1,2-benzisoxazole-3-carboxamide; and
trans-N-[3-[3-methyl-1-(4-phenyl-1-piperazinyl) cyclohexyl]phenyl]-1,2-benzisoxazole-3-carboxamide.

10. An amido NPY antagonist selected from the group consisting of:
cis-5-chloro-N-[3-[4-methyl-1-(4-phenyl-1-piperazinyl) cyclohexyl]phenyl]-1H-indazole-3-carboxamide;
cis-5-chloro-N-[3-[4-methyl-1-(4-(4-flurophenyl-1-piperazinyl) cyclohexyl]phenyl]-1H-indazole-3-carboxamide;
cis-N-[3-[4-methyl-1-(4-phenyl-1-piperazinyl) cyclohexyl]phenyl]-1H-indazole-3-carboxamide;
trans-N-[3-[3-methyl-1-(4-phenyl-1-piperazinyl) cyclohexyl]phenyl]-1H-indazole-3-carboxamide; and
cis-5-methyl-N-[3-[4-methyl-1-(4-(4-fluorophenyl-1-piperazinyl) cyclohexyl]phenyl]-1H-indazole-3-carboxamide.

11. An amido NPY antagonist selected from the group consisting of:
cis-N-[3-[4-methyl-1-(4-phenyl-1-piperazinyl) cyclohcxyl]phenyl]-1H-indole-3-carboxamide; and
cis-5-chloro-N-[3-[4-methyl-1-(4-phenyl-1-piperazinyl) cyclohexyl]phenyl]-1H-indole-3-carboxamide.

12. An amido NPY antagonist selected from the group consisting of:
cis-N-[3-[4-methyl-1-(4-phenyl-1-piperazinyl) cyclohexyl]phenyl]-2-quinoxalinecarboxamide; and
cis-N-[3-[4-methyl-1-(4-(4-fluoroplienyl-1-piperazinyl) cyclohexyl]phenyl]-2-quinoxalinecarboxamide.

13. An amido NPY antagonist selected from the group consisting of:
cis-N-[3-[4-methyl-1-(4-phenyl-1-piperazinyl) cyclohexyl]phenyl]-1-naphthalenecarboxamide; and
cis-N-[3-[4-methyl-1-(4-phenyl-1-piperazinyl) cyclohexyl]phenyl]-2-naphthalenecarboxamide.

14. An amido NPY antagonist selected from the group consisting of:
cis-N-[3-[4-methyl-1-(4-phenyl-1-piperazinyl) cyclohexyl]phenyl]-4-pyrazolocarboxamide; and
cis-N-[3-[4-methyl-1-(4-phenyl-1-piperazinyl) cyclobexyl]phenyl]-2-pyrazinylcarboxamide.

15. An amido NPY antagonist selected from the group consisting of:
cis-N-[3-[4-methyl-1-(4-phenyl-1-piperazinyl) cyclohexyl]phenyl]-4-nitrobenzamide; and
cis-N-[3-[4-methyl-1-(4-phenyl-1-piperazinyl) cyclohexyl]phenyl]-4-aminobenzamide.

16. A sulfonamide NPY antagonist selected from the group consisting of:
cis-N-1-[3-(1,1-dioxoisothiazolidin-2-yl) -phenyl]-1-4 [(4-fluorophenyl)pipcrazin-1-yl]-4-methyl cyclohexane;
cis-N-[3-[4-methyl-1-(4-phenyl-1-piperazinyl) cyclohexyl]phenyl]-2-naphthalenesulfonamide;
cis-N-[3-[4-methyl-1-(4-phenyl-1-piperazinyl) cyclohexyl]phenyl]-methanesulfonamide; and
cis-N-[3-[4-methyl-1-(4-phenyl-1-piperazinyl) cyclohexyl]phenyl]-toluenesulfonamide.

* * * * *